(12) United States Patent
Kato (10) Patent No.: US 8,976,361 B2
(45) Date of Patent: Mar. 10, 2015

(54) REFLECTION CHARACTERISTIC MEASURING APPARATUS

(71) Applicant: Canon Kabushiki Kaisha, Tokyo (JP)

(72) Inventor: Shigeki Kato, Shimotsuke (JP)

(73) Assignee: Canon Kabushiki Kaisha (JP)

( * ) Notice: Subject to any disclaimer, the term of this patent is extended or adjusted under 35 U.S.C. 154(b) by 0 days.

(21) Appl. No.: 14/138,369

(22) Filed: Dec. 23, 2013

(65) Prior Publication Data

US 2014/0176953 A1 Jun. 26, 2014

(30) Foreign Application Priority Data

Dec. 25, 2012 (JP) ................................ 2012-281756

(51) Int. Cl.
*G01N 21/55* (2014.01)
*G01N 21/17* (2006.01)
*G01N 21/47* (2006.01)
*G01N 21/57* (2006.01)

(52) U.S. Cl.
CPC ............ *G01N 21/4738* (2013.01); *G01N 21/55* (2013.01); *G01N 21/57* (2013.01); *G01N 2021/556* (2013.01)
USPC .......................................... 356/445; 356/448

(58) Field of Classification Search
USPC .................. 356/445–448, 450–458
See application file for complete search history.

(56) References Cited

U.S. PATENT DOCUMENTS 6,733,105 B2 * 5/2004 Tatsumi ........................ 347/21
7,292,375 B2 * 11/2007 Nishida ........................ 358/3.26
8,537,421 B2 * 9/2013 Itoh et al. ..................... 358/1.9
8,711,171 B2 * 4/2014 Sano ............................ 345/593
2008/0246969 A1 10/2008 Imura

FOREIGN PATENT DOCUMENTS

JP 2007-024655 A 2/2007
JP 2008-256454 A 10/2008

OTHER PUBLICATIONS

Frederic Leloup, et al.; "Design of an instrument for measuring the spectral bidirectional scatter distribution function"; Applied OPTICS/vol. 47, No. 29/ Oct. 10, 2008. pp. 5454-5467.
Extended European Search Report for corresponding EP 13197240.8, mail date Apr. 3, 2014.

* cited by examiner

*Primary Examiner* — Kara E Geisel
*Assistant Examiner* — Jarreas C Underwood
(74) *Attorney, Agent, or Firm* — Rossi, Kimms & McDowell LLP

(57) ABSTRACT

A measuring apparatus includes an illumination device including a surface light source, a detector configured to detect a light intensity distribution formed on a light-receiving surface by reflected light, and a processor configured to obtain the reflection characteristic based on first data of the light intensity distribution detected by the detector. The processor is configured to estimate, based on the first data, second data of a light intensity distribution formed by specular reflected light and third data of a light intensity distribution formed by diffuse reflected light in a case where a point light source is disposed at each position in a light-emitting region of the surface light source, and to estimate, based on the second data and the third data, a light intensity distribution formed by reflected light from the surface.

13 Claims, 5 Drawing Sheets

BRDF1A
(SPECULAR REFLECTED LIGHT
COMPONENT)

BRDF1B
(DIFFUSE REFLECTED LIGHT
COMPONENT)

} BRDF1

F I G. 4

F I G. 5

FIG. 6
PRIOR ART (JIS Z 8741)

FIG. 7
PRIOR ART (ASTM E 430)

FIG. 8
PRIOR ART (JIS K 7374)

REFLECTION CHARACTERISTIC MEASURING APPARATUS

BACKGROUND OF THE INVENTION

1. Field of the Invention

The present invention relates to a measuring apparatus for measuring a reflection characteristic of a surface.

2. Description of the Related Art

Conventionally, it is an important proposition to evaluate a printed product, a painted surface, and an exterior of a product, and JIS and ISO set standards for measuring a reflection characteristic of an object surface (surface) such as gloss. For example, as standards for measuring a specular gloss, JIS Z 8741 and the like are set. As standards for measuring a haze which represents a degree of image unclearness (dullness of a sample surface), ISO13803, ASTM E 430, and the like are set. As standards for measuring distinctness-of-image gloss associated with gloss, ASTM E 430, ASTM D 5767, and the like are set. As standards for measuring an image clarity (image clearness), JIS K 7374, JIS H 8686, and the like are set.

Figure 6:
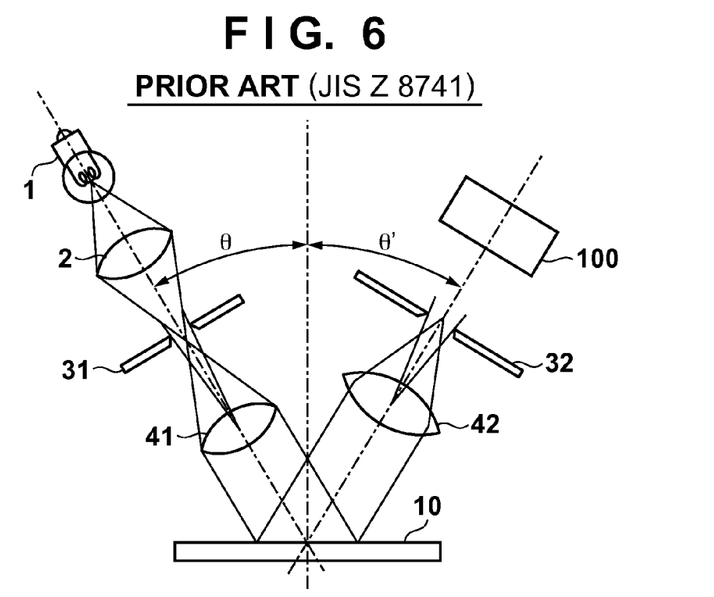
FIG. 6 is a view showing the arrangement of a specular gloss measuring apparatus designated, by JIS Z 8741.

In respective standards, since there are surfaces suitable and unsuitable for measurement, the user has to select an optimal standard from the aforementioned standards depending on the situation, so as to measure the reflection characteristic. FIG. 6 shows a specular gloss measuring method defined in JIS Z 8741. A light beam from a light source 1 is roughly condensed by a lens 2 to be condensed on a rectangular light source slit 31, which is set to have an aperture angle defined by the standard, and the light source slit 31 forms a secondary light source having the defined aperture angle. A light beam from the light source slit 31 is converted into a nearly parallel light beam by a lens 41, and a surface 10 is irradiated with the nearly parallel light, beam. Light reflected by the surface 10 has a unique reflection pattern depending on a state of the surface 10, and is condensed again by a lens 42, thus forming an image of the light source slit 31 on a light-receiving slit 32. Light, which has passed through the light-receiving slit 32, enters a light-receiving element 100, and is output as a photoelectric signal from the light-receiving element 100. A specular gloss measuring apparatus shown in FIG. 6 calculates a glossiness of the surface 10 using a relative intensity between the amount of light reflected by the surface 10 and an amount of light reflected by a reference surface, which amount is measured in advance. The specular gloss measuring apparatus shown in FIG. 6 can define brightness of reflection of a light source, but does not define a blurted degree of reflection of a light source, and cannot perfectly express the state of the surface 10.

Figure 7:
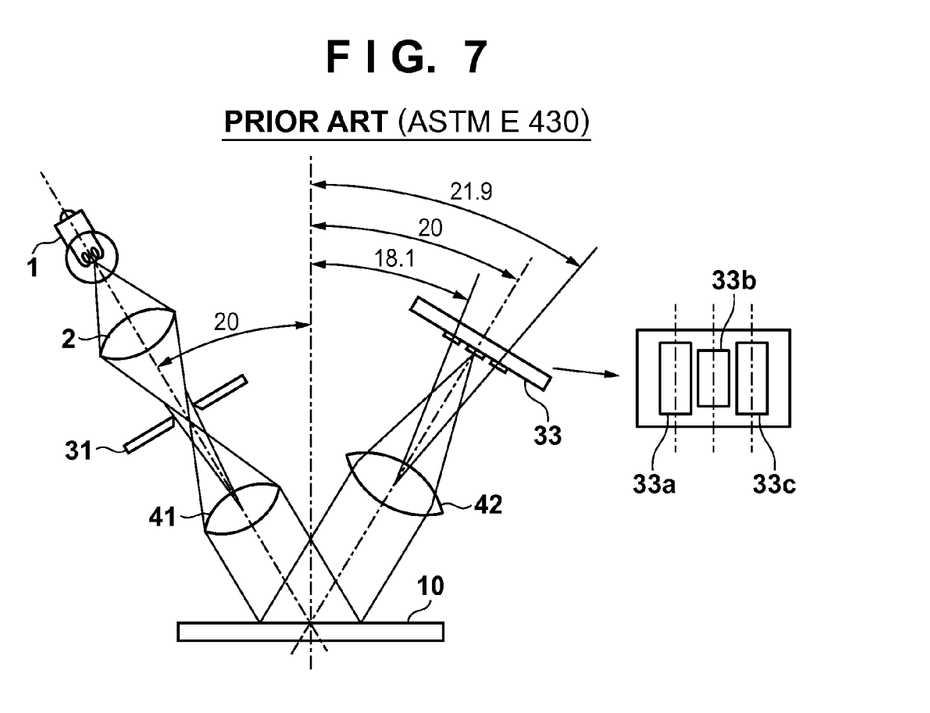
FIG. 7 is a view showing the arrangement of a haze measuring apparatus designated by ASTM E 430.

FIG. 7 shows the arrangement of an apparatus for measuring a haze defined by ASTM E 430. A light beam from a light source 1 is roughly condensed by a lens 2 to be condensed on a light source slit 31, which is set to have an aperture angle defined by the standard, and the light source slit 31 forms a secondary light source having the defined aperture angle. A light beam from the light source slit 31 is converted into a nearly parallel light beam by a lens 41, and a surface 10 is irradiated with the nearly parallel light beam. Light reflected by the surface 10 has a unique reflection pattern depending on a state of the surface 10, and is condensed again by a lens 42, thus forming an image of the light source slit 31 on a light-receiving slit 33. Light, which has passed through the light-receiving slit 33, enters a light-receiving element, and is output as a photoelectric signal. The light-receiving slit 33 includes three slits 33a, 33b, and 33c, which are set at 18.1°, 20°, and 21.9° with respect to a perpendicular to the surface 10. The slit 33b is used to measure a specular gloss, and the slits 33a and 33c are used to measure a haze. The haze is an index indicating a degree of image unclearness. However, since an angle difference from specular reflected light of the slits 33a and 33c is small, a state of the surface 10 suitable for measurement of a haze is limited. When a reflection image exhibits unclearness beyond recognition, it is difficult to calculate a haze from the measurement result of the measuring apparatus shown in FIG. 7.

A distinctness-of-image gloss is measured using an apparatus having the same arrangement as that shown in FIG. 7 except for dimensions of the slits and a value calculation formula. More specifically, angles of the slits 33a, 33b, and 33c with respect to the perpendicular to the surface 10 are 19.7°, 20°, and 20.3°, and slit sizes are different. Like in measurement of a haze and the like, it is difficult for the surface 10 whose reflection image exhibits unclearness beyond recognition to calculate a distinctness-of-image gloss.

Figure 8:
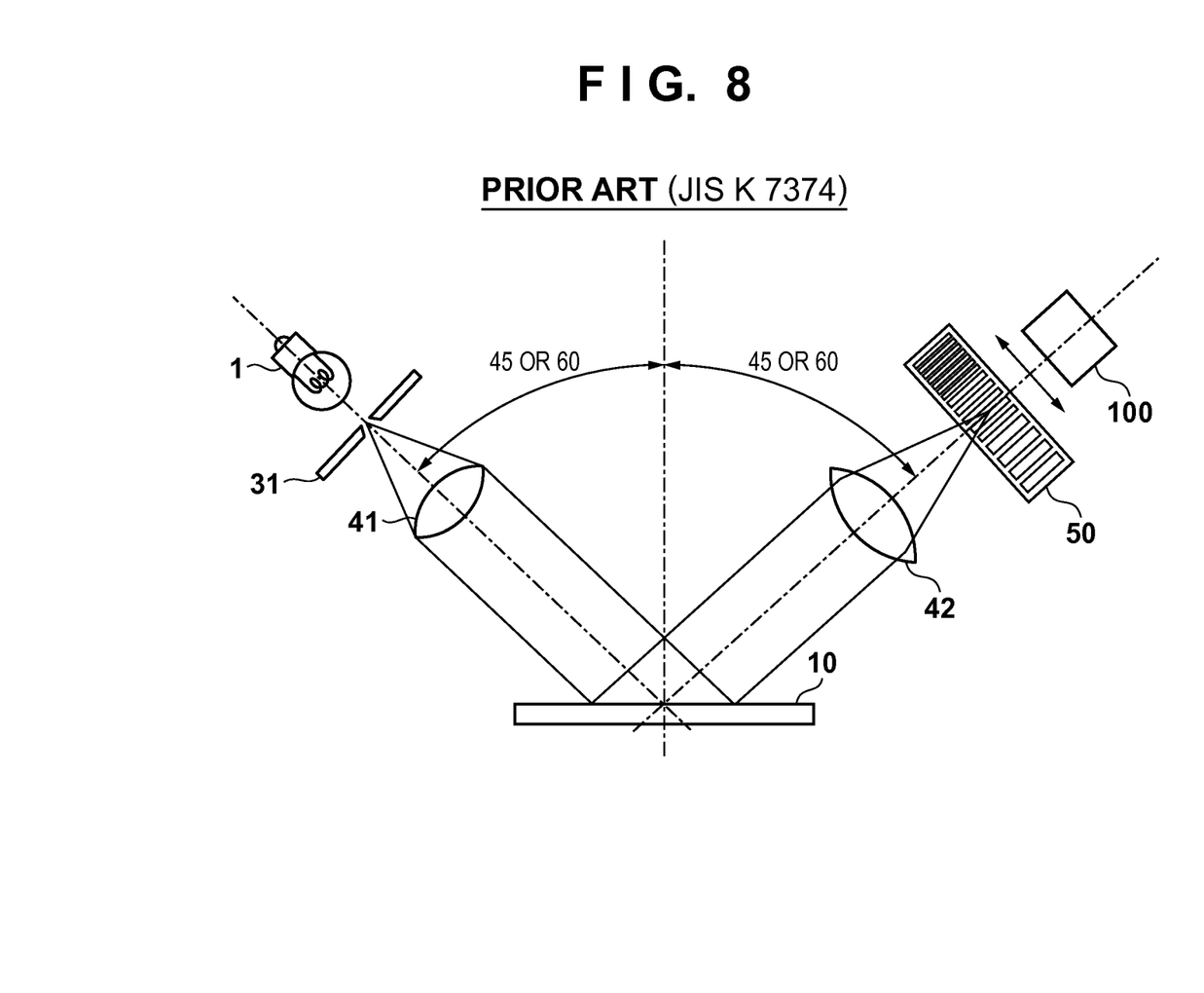
FIG. 8 is a view showing the arrangement, of an image clarity measuring apparatus designated by JIS K 7374.

FIG. 8 shows the arrangement of an apparatus used in an image clarity test method defined by JIS K 7374. A light beam from a light source 1 passes through a slit 31 and enters a lens 41 to be converted into parallel light, with which a surface 10 is irradiated. Reflected light by the surface 10 has a unique reflection pattern depending on a state of the surface 10, and is condensed again by a lens 42, thus forming an image of the light source slit 31 on a comb-tooth slit 50. The comb-tooth slit 50 is configured by five types of slits having different pitches. Contrast values are acquired by calculating maximum and minimum transmitted light amounts upon moving the comb-tooth slit 50 in a slit array direction, thus expressing the state of the surface 10 by five contrast values. Since the image clarity measuring method evaluates the clearness of a reflection image using contrast values, the brightness of the reflection image cannot be discussed.

Japanese Patent Laid-Open No. 2008-256454 describes an apparatus and method for measuring a specular gloss of a surface, and Japanese Patent Laid-Open No. 2007-24655 describes an apparatus and method for measuring an image clarity of a surface.

As described above, the measuring apparatuses defined by the respective standards have respective features, and measure different target reflection characteristics of a surface. Also, Japanese Patent Laid-Open Nos. 2008-256454 and 2007-24655 disclose the apparatuses and methods for measuring reflection characteristics of a surface. However, these apparatuses and methods can only measure limited reflection characteristics of the surface. Therefore, the user in need of various reflection characteristics of a surface, has to prepare for measuring apparatuses of a plurality of methods, and has to selectively use them depending on the situation. For this reason, the user requires cost for purchasing a plurality of apparatuses, and a place for housing the plurality of apparatuses, thus imposing a load on the user.

SUMMARY OF THE INVENTION

The present invention provides, for example, a technique which enables a single measuring apparatus to measure a plurality of types of reflection characteristics of a surface.

The present invention provides a measuring apparatus for measuring a reflection characteristic of a surface, the measuring apparatus comprising: an illumination device including a surface light source and configured to illuminate the surface with light from the surface light source; a detector configured to detect a light intensity distribution formed on a light-receiving surface by reflected light from the surface illuminated by the illumination device; and a processor configured to obtain the reflection characteristic based on first data of the light intensity distribution detected by the detector, wherein the processor is configured to estimate, based on the first data, second data of a light intensity distribution formed on the light-receiving surface by specular reflected light from the surface and third data of a light intensity distribution formed on the light-receiving surface by diffuse reflected light from the surface in a case where a point light source is disposed at each position in a light-emitting region of the surface light source, and to estimate, based on the second data and the third data, a light intensity distribution formed on the light-receiving surface by reflected light from the surface in a case where a light source, at least one of a shape and a size of a light-emitting region of which is different from that of the surface light source, is disposed in place of the surface light source.

Further features of the present invention will become apparent from the following description of embodiments with reference to the attached drawings.

DESCRIPTION OF THE EMBODIMENTS

Embodiments of the present invention will be described in detail hereinafter with reference to the accompanying drawings.

[First Embodiment]

Figure 1:
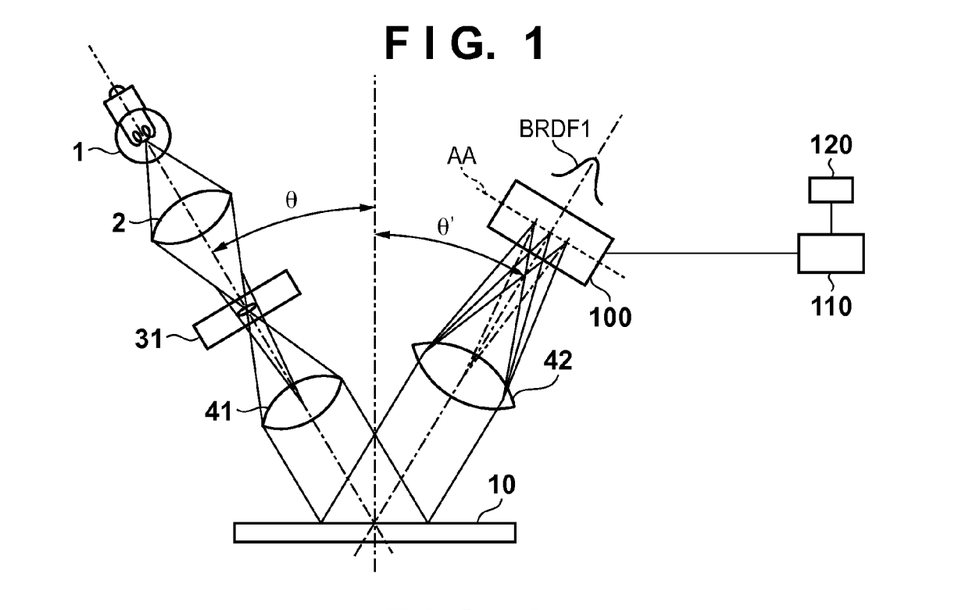
FIG. 1 is a schematic view showing the arrangement of a measuring apparatus according to the first embodiment.

FIG. 1 shows a schematic arrangement of a measuring apparatus for measuring a reflection characteristic of a surface according to the first embodiment. An illumination device from a light source 1 to a lens 41 and a light-receiving device from a lens 42 to a two-dimensional light-receiving element (detector) 100 are disposed to respectively have angles θ and θ' with respect to a perpendicular to a surface 10. The incident angle θ and reflection angle θ' are set for each standard to be compliant with that standard which defines a reflection characteristic of the surface 10. When a reflection characteristic is a specular gloss, the incident angle θ and light-receiving angle θ' are set at any of 20°, 45°, 60°, and 85°. When a reflection characteristic is a haze, the incident angle θ and reflection angle θ' are set at 20°. When a reflection characteristic is an image clarity, the incident angle θ and reflection angle θ' are set at any of 45° and 60°. When a reflection characteristic is a distinctness-of-image gloss, the incident angle θ and reflection angle θ' are set at 20°.

A light beam emitted from the light source 1 is condensed on a stop 31 having a circular aperture of ϕ1 mm by a lens 2. On the stop 31, an image of the light source 1 is temporarily formed as a circular secondary light source (surface light source) of ϕ1 mm. A light beam emitted from the stop 31 becomes a diverging light beam again, and is converted into parallel light by the lens 41, thus illuminating the surface 10. Reflected light from the surface 10 has a unique reflection pattern depending on the reflection characteristic of the surface 10, and is received by a light-receiving surface of the two-dimensional light-receiving element 100. The two-dimensional light-receiving element 100 detects an intensity distribution of light formed on the light-receiving surface by the reflected light form the surface 10, and outputs first data to a processor 110. More specifically, the first data is a reflection pattern like a BRDF 1 with which an intensity changes according to an angle. Note that the BRDF (Bidirectional Reflectance Distribution Function) is a function which expresses a reflectance distribution of the surface 10, and represents a ratio of reflected light luminance to incident light illuminance. More strictly, a BRDF at a certain point on an object surface depends on two directions, that is, incident and reflection directions, and is defined as a ratio of an intensity of reflected light in an observation direction to that of incident light from an illumination direction. A signal received by the two-dimensional light-receiving element 100 can express a reflection characteristic unique to the surface 10 by trimming an output along an AA section on the two-dimensional light-receiving element 100.

Figure 2:
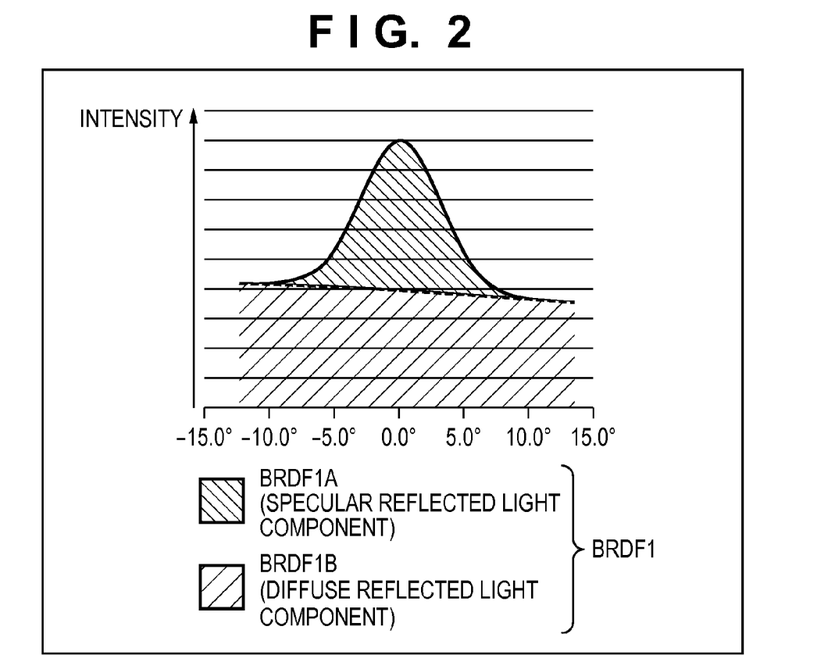
FIG. 2 is a graph showing an intensity distribution when specular reflected light and diffuse reflected light are combined.

The intensity distribution of reflected light received by the two-dimensional light-receiving element 100 is trimmed along the AA section to cope with calculations of the respective standards which define the reflection characteristics. When the intensity distribution of reflected light is trimmed along another section in addition to the AA section, an anisotropy of the reflection characteristic of the surface 10 can also be measured. The reflection pattern BRDF 1 received by the two-dimensional light-receiving element 100 is obtained by combining a BRDF 1A by specular reflected light and a BRDF 1B by diffuse reflected light, as shown in FIG. 2. The specular reflected light is also called surface reflected light, and the diffuse reflected light is also called scattered light. Since the BRDF 1B by diffuse reflected light corresponds to so-called a background color and brightness of the surface 10, and seems to have equal brightness independently of a visual line angle, the brightness is expressed by a model which is proportional to COS θ with respect to a visual line angle θ, and is called Lambert scattering. The BRDF 1A by specular reflected light corresponds to a state of reflection of the light source 1, is normally modeled by a Gaussian distribution, and is defined by a spread degree and intensity of the distribution as parameters.

Figure 3:
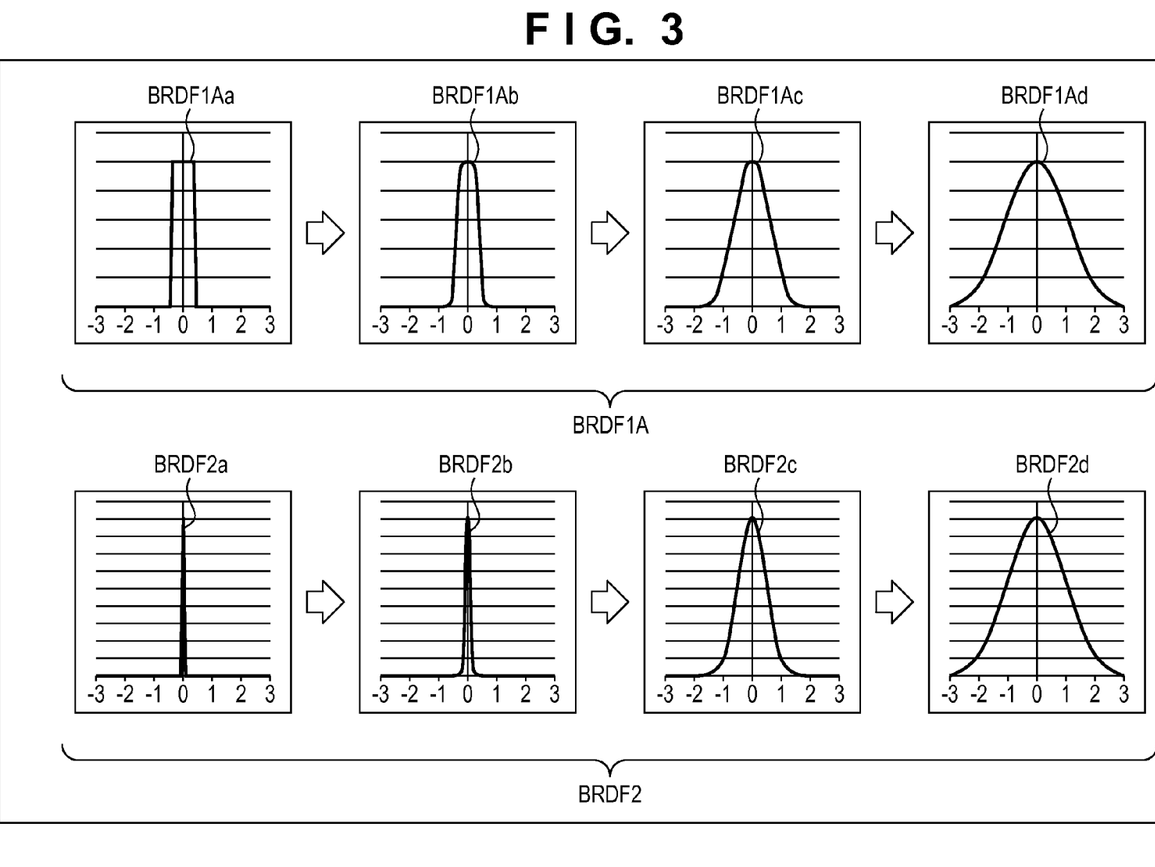
FIG. 3 shows graphs of a transition of intensity distributions of specular reflected light in case of a circular aperture, and that of intensity distributions of specular reflected light in case of a point light source.

In this case, attention will be focused on the BRDF 1A based on the specular reflected light obtained by the two-dimensional light-receiving element 100 using the stop 31 having the circular aperture. The light intensity distribution BRDF 1A by specular reflected light when the circular aperture is used changes from a BRDF 1Aa to a BRDF 1Ad during processes in which the surface 10 transits from a specular surface to a scattering surface, as shown in FIG. 3. When the surface 10 is a specular surface, since the circular aperture of the stop 31 is projected intact on the two-dimensional light-receiving element 100, a rectangular BRDF 1Aa with a sharp edge is output. During processes in which the surface 10 becomes closer to a diffusing surface, the rectangular shape is broken, and a nearly Gaussian distribution like a BRDF 1Ad is finally output.

Assume that four surfaces 10 which exhibit reflection patterns of BRDFs 1Aa to 1Ad by specular reflected light when the surface 10 is irradiated with light using the stop 31 having the circular aperture will be respectively referred to as surfaces 10a to 10d. Assume that BRDFs 2 by specular reflected light obtained by the two-dimensional light-receiving element 100 when a point light source (for example, a light source of φ10 μm) is disposed at one of a plurality of positions in a plane of the stop 31 and the surfaces 10a to 10d are illuminated with light coming from that light source will be respectively referred to as BRDFs 2a to 2d. The BRDFs 2a to 2d are simple Gaussian distribution patterns in which only a spread degree and intensity are changed during transition processes from specular surfaces to scattering surfaces of the surfaces 10a to 10d. The BRDFs 2a to 2d can be estimated from addition calculations under the assumption that the circular aperture of the stop 31 is a set of point light sources. Alternatively, the BRDFs 2a to 2d can be calculated via actual measurements by arranging a point light source at each of the plurality of positions in the plane of the stop 31. In the first embodiment, information indicating the relationship between the BRDFs 1Aa to 1Ad and the BRDFs 2a to 2d is acquired in advance by calculations or actual measurements, and is stored in a memory 120 of the measuring apparatus.

When the BRDFs 2a to 2d are to be calculated, for example, a size φ of a point light source is set to fall within a range of several μm to several ten μm, and a blurred pattern on the two-dimensional light-receiving element 100 is modeled by being approximated to a Gaussian distribution. Assuming that the circular aperture of the stop 31 is a set of point light sources, a blurred image of the circular aperture on the two-dimensional light-receiving element 100 can be assumed to be a set of blurred images of the point light sources. Sum totals of light intensities obtained from the respective point light sources as many as the numbers of point light sources on a plane coordinate system on the two-dimensional light-receiving element 100 are equal to the BRDFs 1Aa to 1Ad. Based on the aforementioned principle, the BRDFs 2a to 2d can be calculated (back-calculated) from actually measured values of the BRDFs 1Aa to 1Ad.

The BRDF 1A by specular reflected light when the stop 31 having the circular aperture is used and the reflection pattern BRDF 2 of a point light source can be associated with each other using, for example, a half width and peak ratio of the reflection pattern. Also, since the half width of the reflection pattern is not monotonically increased near specular reflection during blurring processes of an image, the BRDF 1A may be associated with the BRDF 2 using a width other than the half width, for example, a ⅓ width of a peak. The width of the peak used in association with the BRDF 2 may be other widths such as a ¼ width in addition to the ⅓ width. However, when the width of the peak used in association with the BRDF 2 falls below a ⅕ width, a boundary between specular reflected light and diffuse reflected light (scattered light) becomes unspecific, and an inclination of a Gaussian distribution waveform becomes moderate, thus readily causing errors. Alternatively, a correlation of maximum values (peaks of differential waveforms) of inclination values of profiles of the BRDFs 2a to 2d and BRDFs 1Aa to 1Ad or that of distances between maximum values of inclinations of profiles may be calculated, or a correlation may be calculated by combining them. With the aforementioned method, the processor 110 can calculate the reflection pattern BRDF 2 of the point light source from the BRDF 1A.

For example, assume that a pinhole of φ10 μm is actually disposed as a point light source at a position of the circular aperture of the stop 31. Then, the obtained light amount is only about 1/10000 of that obtained when the stop 31 having the circular aperture is used. For this reason, it becomes difficult to precisely measure reflection profiles, or an accumulation time of the two-dimensional light-receiving element 100 has to be prolonged, resulting in a low throughput. Therefore, it is very effective to dispose the stop 31 having the circular aperture of φ1 μm or more, and to calculate the reflection pattern BRDF 2 of the point light source by calculations in terms of signal quality. In the first embodiment, the processor 110 divides the BRDF 1 into the BRDF 1A by specular reflected light and the BRDF 1B by diffuse reflected light, and then calculates a correlation between the BRDF 1A and the reflection pattern BRDF 2 by specular reflected light of the point light source.

However, the processor 110 may estimate, based on the BRDF 1, data of the light intensity distribution formed on the light-receiving surface by reflected light when a point light source is disposed at one of a plurality of positions of the circular aperture of the stop 31. The processor 110 can calculate the BRDF 2 (second data) by specular reflected light and a BRDF 3 (third data) by diffuse reflected light by dividing the estimated data. In this case, the processor 110 can calculate the BRDF 3 based on the BRDF 1B by diffuse reflected light and a ratio between the size of the point light source and the circular aperture of the stop 31.

The BRDF 1B by diffuse reflected light will be described below. As is known, diffuse reflected light can be modeled by being approximated to Lambert scattering. The Lambert scattering defines that a reflected light amount ratio to an angle θ is COS θ based on the fact that the brightness of object on a perfectly diffusing surface (perfect diffuse surface or Lambertian surface) is constant independently of a visual line. When a BRDF based on reflected light generated by a reference surface having a given diffuse reflectance (diffuse reflected light/incident light) is measured in advance using this measuring apparatus, the BRDF 3 based on the BRDF 1B by diffuse reflected light can be estimated by giving parameters of the diffuse reflectance. Since levels of specular reflected light and diffuse reflected light to be mixed are determined by an area of the light source 1, the diffuse reflectance and the area of the light source 1 can be used in calculations to be described later when they are stored in the memory 120.

A process for calculating standard values of various reflection characteristics defined by arbitrary measuring conditions from the reflection pattern BRDF 2 of the point light source derived in the above processes will be described below. A measuring condition of a settable reflection characteristic includes a shape and size of an arbitrary light source, an arbitrary evaluation region on the light-receiving surface, an incident angle of parallel light, and the like.

For example, assume that a glossimeter described in JIS Z 8741 of a specular gloss is configured. The processor 110 calculated the BRDF 2 by specular reflected light in case of φ10 μm in the above processes. When a specular gloss is to be measured at an incident angle of 20°, an aperture on the light source side is a rectangle having a width of 0.75° and a length of 2.5°, which are defined by an aperture angle. Using a focal length F of the lens 41 and an aperture angle β, a size of the aperture on the light source side can be calculated by F×COS β. Therefore, if the focal length is 50 mm, it can be calculated that a rectangular slit having a width of 0.65 mm and a length of 2.18 mm is required as the aperture on the light source side.

A reflection pattern by specular reflected light on the two-dimensional light-receiving element 100 when this rectangular slit is used can be calculated by the processor 110 by adding light amounts on a two-dimensional space to have the rectangular slit of the width of 0.65 mm and the length of 2.18 mm as a set of point light sources of φ10 μm. The light intensity distribution by diffuse reflected light when this rectangular slit is used can be calculated by multiplying the divided BRDF 1B by an area ratio $0.65 \times 2.18 \div (\pi \times 0.5^2) = 1.8$ of the rectangular slit with respect to the circular aperture. In this manner, a calculated reflected light pattern on the two-dimensional light-receiving element 100 when the apparatus arrangement of the specular gloss measuring method is adopted can be obtained by the measuring apparatus of the first embodiment. In order to output a standard value of JIS Z 8741, a light amount, which enters a light-receiving side area having a width of 1.8° and a length of 3.6°, which are defined by an aperture angle, has to be calculated. However, that light amount can be easily calculated from the calculated reflected light pattern on the two-dimensional light-receiving element 100.

The measurement of the specular gloss has been Explained. However, as for haze and distinctness-of-image gloss measurements, similar calculations can be made. As for an image clarity measurement, a comb-tooth slit defined in the JIS K 7374 standard is assumed as a light-receiving area assumed on the two-dimensional light-receiving element 100. An image clarity can be calculated from maximum and minimum transmitted light amounts during a moving process of the assumed light-receiving area by one slit pitch. When a light, irradiation direction in the measuring apparatus is configured to be changed to 20°, 45°, 60°, and 85° like in a conventionally manufactured specular gloss measuring apparatus, evaluation values specified in various standards in association with a specular gloss, haze, image clarity, and distinctness-of-image gloss can be acquired by a single measuring apparatus.

As described above, since the measuring apparatus of the first embodiment can acquire various reflection characteristics of the surface 10, the user need not selectively use a plurality of apparatuses depending on types of reflection characteristics. Also, since the measuring apparatus of the first embodiment uses, as the light source 1, a light source having a certain size in place of a point light source, it is effective in terms of S/N, thus allowing measurements within a short period of time.

[Second Embodiment]

Figure 4:
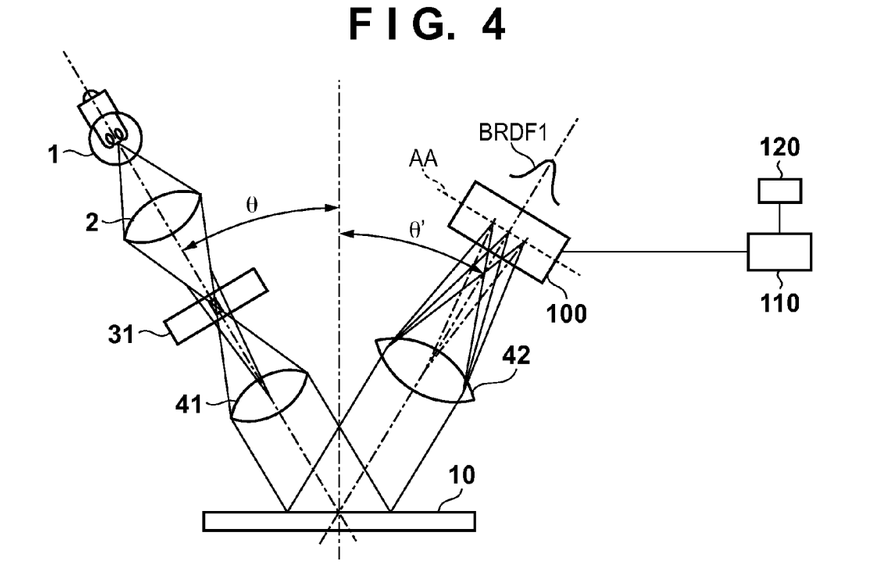
FIG. 4 is a schematic view showing the arrangement of a measuring apparatus according to the second embodiment.

FIG. 4 shows a schematic arrangement of a measuring apparatus according to the second embodiment. Unlike in the first embodiment, a stop 31 has a rectangular slit in place of a circular aperture. The rectangular slit of the stop 31 has an aperture angle of 0.75° in a widthwise direction and that of 2.5° in a lengthwise direction, which are defined in the standard required to measure a specular gloss. For this reason, by adding outputs of an element of an aperture angle on the light-receiving device side, which is designated by the standard, on a two-dimensional light-receiving element 100, a specular gloss which matches the standard of a specular gloss measuring method can be easily acquired. Likewise, as for a haze measurement, since the aperture angle on the light source side, which is designated by the standard, is the same, a haze can be easily acquired.

On the other hand, in the same manner as in the process described using FIG. 3 of the first embodiment, a reflection pattern BRDF 2 of a point light source can be calculated or associated by advanced measurements from a BRDF 1A by specular reflected light upon trimming along an AA section of the two-dimensional light-receiving element 100. Therefore, even when the measuring apparatus of the second embodiment is used, an image clarity can be measured. The measuring apparatus of the second embodiment requires a smaller calculation volume than that of the first embodiment, and is further effective in that the apparatus arrangement perfectly matches the standard upon measuring a specular gloss and haze. The measuring apparatus of the second embodiment can cope with measurements in only one direction. Hence, a one-dimensional light-receiving element may be disposed in a direction of AA in place of the two-dimensional light-receiving element 100. In this case, since a data amount is greatly reduced, a load on signal processing can be reduced.

[Third Embodiment]

Figure 5:
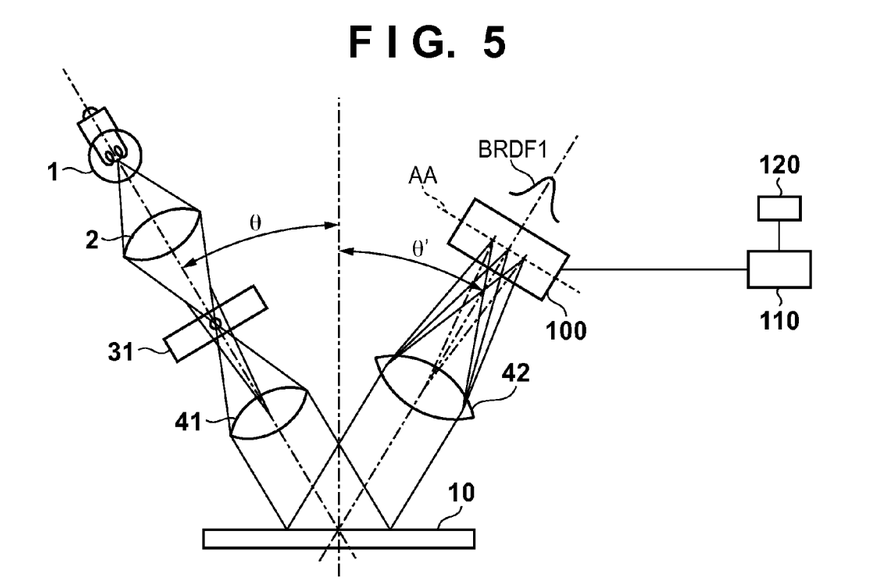
FIG. 5 is a schematic view showing the arrangement of a measuring apparatus according to the third embodiment.

FIG. 5 shows a schematic arrangement of a measuring apparatus according to the third embodiment. Unlike in the first and second embodiments, a stop 31 has a hexagonal aperture in place of a circular aperture or rectangular slit. In this case, reflection patterns in three directions perpendicular to three pairs of sides of a hexagon can be measured. Like in the first and second embodiments, a specular gloss, haze, and image clarity can be measured. Since the measuring apparatus of the third embodiment can measure reflection patterns in two directions different from an AA section, in addition to measurements that match the standards it can also make determination when a reflection pattern has an anisotropy. In the third embodiment, the stop 31 has a hexagonal aperture, but it may have an n-sided polygonal aperture other than the hexagonal aperture. The n-sided polygon is desirably an even-sided polygon (especially, a regular even-sided polygon) in terms of symmetry.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-281756 filed Dec. 25, 2012, which is hereby incorporated by reference herein in its entirety.

What is claimed is:

1. A measuring apparatus for measuring a reflection characteristic of a surface, the measuring apparatus comprising:
    an illumination device including a surface light source and configured to illuminate the surface with light from the surface light source;
    a detector configured to detect a light intensity distribution formed on a light-receiving surface by reflected light from the surface illuminated by said illumination device; and
    a processor configured to obtain the reflection characteristic based on first data of the light intensity distribution detected by said detector,
    wherein said processor is configured to estimate, based on the first data, second data of a light intensity distribution formed on the light-receiving surface by specular reflected light from the surface and third data of a light intensity distribution formed on the light-receiving surface by diffuse reflected light from the surface in a case where a point light source is disposed at each position in a light-emitting region of the surface light source, and to estimate, based on the second data and the third data, a light intensity distribution formed on the light-receiving surface by reflected light from the surface in a case where a light source, at least one of a shape and a size of a light-emitting region of which is different from that of the surface light source, is disposed in place of the surface light source.

2. The apparatus according to claim 1, wherein said processor is configured to obtain, based on the second data and the third data, a light intensity distribution formed on an evaluation area set with respect to the light-receiving surface.

3. The apparatus according to claim 2, wherein a measuring condition, settable in the apparatus, includes at least one of the shape, the size, and the evaluation area.

4. The apparatus according to claim 1, wherein the surface light source is a circular light source, and said detector includes a two-dimensional light-receiving element array.

5. The apparatus according to claim 1, wherein the surface light source is a rectangular light source, and said detector includes one of a two-dimensional light-receiving element array and a one-dimensional light-receiving element array.

6. The apparatus according to claim 1, wherein the surface light source is an n-sided polygonal light source, and said detector includes a two-dimensional light-receiving element array.

7. The apparatus according to claim 1, wherein the reflection characteristic includes at least one of a specular gloss, a haze, a distinctness-of-image gloss, and an image clarity.

8. The apparatus according to claim 1, wherein said processor is configured to estimate the second data based on a Gaussian distribution, and to estimate the third data based on Lambert scattering.

9. The apparatus according to claim 8, wherein said processor is configured to estimate the third data based on data of a diffuse reflectance of the surface, and data of a light intensity distribution formed on the light-receiving surface with a reference surface having a known diffuse reflectance as a surface to be measured.

10. The apparatus according to claims 1, wherein said processor is configured to estimate, based on the first data, data of a light intensity distribution formed on the light-receiving surface by reflected light from the surface in a case where a point light source is disposed at each position in a light-emitting region of the surface light source, and to obtain the second data and the third data by dividing the estimated data.

11. The apparatus according to claim 1, wherein said processor is configured to divide the first data into data of a specular reflected light intensity distribution and data of a diffuse reflected light intensity distribution, and to estimate the second data and the third data respectively based on the two data obtained by the division.

12. The apparatus according to claim 11, wherein said processor is configured to estimate the third data based on the data of the diffuse reflected light intensity distribution, and a ratio between a size of the point light source and a size of the surface light source.

13. The apparatus according to claim 11, wherein said processor is configured to estimate the second data based on information indicating a relation between the specular reflected light intensity distribution and the second data, and the data of the specular reflected light intensity distribution.

* * * * *